(12) United States Patent
Malshe et al.

(10) Patent No.: US 9,682,170 B2
(45) Date of Patent: Jun. 20, 2017

(54) NANOSTRUCTURED HYDROXYAPATITE COATING FOR DENTAL AND ORTHOPEDIC IMPLANTS

(75) Inventors: Ajay P. Malshe, Springdale, AR (US); Wenping Jiang, Fayetteville, AR (US)

(73) Assignees: The Board of Trustees of the University of Arkansas, Little Rock, AR (US); NanoMech, Inc., Springdale, AR (US)

( * ) Notice: Subject to any disclaimer, the term of this patent is extended or adjusted under 35 U.S.C. 154(b) by 0 days.

(21) Appl. No.: 13/391,357

(22) PCT Filed: Aug. 20, 2010

(86) PCT No.: PCT/US2010/046158
§ 371 (c)(1),
(2), (4) Date: May 5, 2012

(87) PCT Pub. No.: WO2011/022642
PCT Pub. Date: Feb. 24, 2011

(65) Prior Publication Data
US 2012/0276336 A1 Nov. 1, 2012

Related U.S. Application Data

(60) Provisional application No. 61/235,797, filed on Aug. 21, 2009.

(51) Int. Cl.
*A61L 27/32* (2006.01)
*A61L 27/30* (2006.01)
*A61L 27/56* (2006.01)

(52) U.S. Cl.
CPC ............. *A61L 27/306* (2013.01); *A61L 27/32* (2013.01); *A61L 27/56* (2013.01);
(Continued)

(58) Field of Classification Search
CPC ........ A61L 27/32; A61L 27/56; A61L 27/306; A61L 2400/12; Y10T 428/24413; Y10T 428/24893; Y10T 428/24997
See application file for complete search history.

(56) References Cited

U.S. PATENT DOCUMENTS 6,544,599 B1 4/2003 Brown et al.
6,607,782 B1 8/2003 Malshe et al.
(Continued)

FOREIGN PATENT DOCUMENTS

EP          1656959 A2     5/2006
WO    WO 2007133553 A2 *  11/2007
(Continued)

OTHER PUBLICATIONS

Norhidayu, D.; Sopyan, I.; Ramesh, S.; "Development of Zinc Doped Hydroxyapatite for Bone Implant Applications," 2008, p. 257-270; Presented at ICCBT 2008, Jun. 18, 2008.*
(Continued)

*Primary Examiner* — Mark Ruthkosky
*Assistant Examiner* — Julia L Rummel (57) ABSTRACT

A high-strength coating for dental and orthopedic implants utilizing hydroxyapatite (HAp) nanoparticles provides for a high level of osseointegration through a range of surface pore sizes in the micro- to nanoscale. Zinc oxide (ZnO) nanoparticles may be incorporated with the HAp nanoparticles to form a composite coating material, with ZnO providing infection resistance due to its inherent antimicrobial properties. A textured surface, consisting of "islands" of roughly square coating structures measuring about 250 μm on a side, with spacing of 50-100 μm therebetween, may further promote the osseointegration and antimicrobial properties of the implant coating.

21 Claims, 8 Drawing Sheets

(52) U.S. Cl.
CPC .... *A61L 2400/12* (2013.01); *Y10T 428/24413* (2015.01); *Y10T 428/24893* (2015.01); *Y10T 428/24997* (2015.04)

(56) References Cited

U.S. PATENT DOCUMENTS

| | | | |
|---|---|---|---|
| 2001/0039454 A1* | 11/2001 | Ricci et al. | 623/23.5 |
| 2005/0084608 A1 | 4/2005 | Yadav et al. | |
| 2005/0255239 A1 | 11/2005 | Zhu et al. | |
| 2006/0122706 A1 | 6/2006 | Lo | |
| 2006/0159916 A1 | 7/2006 | Dubrow et al. | |
| 2006/0199013 A1* | 9/2006 | Malshe et al. | 428/409 |
| 2006/0204541 A1* | 9/2006 | Zhang et al. | 424/423 |
| 2007/0142916 A1 | 6/2007 | Olson, Jr. et al. | |
| 2008/0243231 A1* | 10/2008 | Flanagan et al. | 623/1.16 |
| 2009/0035722 A1 | 2/2009 | Balasundaram et al. | |
| 2009/0035723 A1* | 2/2009 | Daniel et al. | 433/215 |
| 2009/0093881 A1* | 4/2009 | Bandyopadhyay et al. | 623/16.11 |
| 2010/0015244 A1* | 1/2010 | Jain | A61L 27/56 424/602 |
| 2010/0131062 A1 | 5/2010 | Andersson et al. | |

FOREIGN PATENT DOCUMENTS

| | | | | |
|---|---|---|---|---|
| WO | WO 2007144667 | A2 | * | 12/2007 |
| WO | WO 2008051433 | A2 | * | 5/2008 |
| WO | 2008070355 | A2 | | 6/2008 |
| WO | WO 2008101011 | A1 | * | 8/2008 ............. A61L 27/10 |

OTHER PUBLICATIONS

Overgaard, S.; Lind, M.; Glerup, H.; Bunger, C.; Saballe, K.; "Porous-Coated Versus Grit-Blasted Surface Texture of Hydroxyapatite-Coated Implants During Controlled Micromotion" Journal of Arthroplasty, 1998, vol. 13, p. 449-458.*

Jaworek, A.; Sobczyk, A. T.; "Electrospraying route to nanotechnology: An overview" Journal of Electrostatics 2008, vol. 66, p. 197-219.*

Wang, R.; Hu, Y; "Patterning hydroxyapatite biocoating by electrophoretic deposition", Journal of Biomedical Materials Research A, 2003, p. 270-275.*

Gilder, "Electron Microscopy Sciences", 2015, p. 1-9, Accessed at on Oct. 27, 2015 at https://www.emsdiasum.com/microscopy/products/grids/gilder.aspx.*

Bandyopadhyay A., Bernard S., Xue W., Bose S., "Calcium Phosphate-Based Resorbable Ceramics: Influence of MgO, ZnO, and SiO2 Dopants," Journal of the American Ceramic Society, vol. 89, pp. 2675 (2006).

Sun, L. et al, 2001, "Material Fundamentals and Clinical Performance of Plasma-Sprayed Hydroxyapatite Coating: A Review," Journal of Biomedical Materials Research, 58(5), pp. 570-592.

Gallardo, J., Galliano, P., Moreno, R., and Duran, A., Journal of Sol-gel Science and Technology, 19, pp. 107-111 (2000).

Huang, J., Jayasinghe, S.N., Best, S. M., Edirisinghe, M.J., Brooks, R. A., Bonfield, W. "Electrospraying of a Nano-Hydroxyapatite Suspension," Journal of Materials Science 39, pp. 1029-1032 (2004).

Jiang, W., Li, S., Gilbert, N., Malshe, A., "Electro Spray Deposition of Nanostructured Hydroxiapatite (HAp) Coating for Biomedical Applications," International Journal for Nanomanufacturing (accepted 2006).

Klabunde KJ, Strak J, Koper O, Mohs C, Park D, Decker S, Jiang Y, Lagadic I, Zhang D. Nanocrystals as stoichiometric reagents with unique surface chemistry. J Phys Chem, vol. 100, pp. 12141 (1996).

Shukla, V., Elliott, G.S., and Kear, B.H., Scripta Materica, 44, pp. 2179-2182 (2001).

Webster TJ, Ergun C, Doremus RH, Siegel RW, Bizios R, "Specific proteins mediate enhanced osteoblast adhesion on nanophase ceramics," J Biomed Mater Res, vol. 52, pp. 475 (2000).

Webster TJ, "Nanophase ceramics: the future of orthopedic and dental implant material," In: Ying JY, editor. Nanostructured Materials, New York: Academy Press; pp. 125-166 (2001).

Webster TJ, Schadler LS, Siegel RW, Bizios R, "Mechanisms of enhanced osteoblast adhesion on nanophase alumina involve vitronectin," Tissue Eng, vol. 7, pp. 291 (2001).

Webster TJ, Ergun C, Dorenus RH, Seigel RW, Bizios R., "Enhanced osteoclast-like functions on nanophase ceramics," Biomaterials, 22:1327-1333 (2001).

Wei, M., Ruys, A.J., Milthorpe, B.K, and Sorrell, C.C., Journal of Biomedical Materials Research, 45(1), pp. 11-19 (1999).

Zhang, Zongtao, Dunn, Mattew F., Xiao, T.D., Tomsia, Atoni P., and Siaz, E., Materials Research Society Proceedings, 703, pp. 291-296 (2002).

Webster, T.J. et al., "Enhanced Functions of Osteoblasts on Nanophase Ceramics," Biomaterials 21(17), pp. 1803-1810.

Liu, H. et al., "Nanomedicine for Implants: a Review of Studies and Necessary Experimental Tools," Biomaterials 28 (2), pp. 354-369.

Xiao, X.F. et al., "Effect of Suspension Stability on Electrophoretic Deposition of Hydroxyapatite Coatings," Materials Letters, 21-22, pp. 2617-2632.

Cheng, G. et al., "Bioceramic Coating of Hydroxyapatite on Titanium Substrate with Nd-YAG Laser," Materials Science and Engineering: C, 25(4), pp. 541-547.

Weng, W. et al, 1998, "Sol-Gel Derived Porous Hydroxyapatite Coatings," Journal of Materials Science: Materials in Medicine, 9(3), pp. 159-163.

European Search Report for European App. No. 10810658.4, dated Mar. 13, 2014.

* cited by examiner

NANOSTRUCTURED HYDROXYAPATITE COATING FOR DENTAL AND ORTHOPEDIC IMPLANTS

CROSS REFERENCE TO RELATED APPLICATIONS

This application is the U.S. National Stage of International Application No. PCT/US2010/046158, filed 20 Aug. 2010, which claims the benefit of U.S. Provisional Application No. 61/235,797, filed 21 Aug. 2009, both of which are incorporated herein by reference.

STATEMENT REGARDING FEDERALLY SPONSORED RESEARCH OR DEVELOPMENT

This invention was made with Government support through NIH Contract No. R43EB003335-01. The Government has certain rights in the invention.

TECHNICAL FIELD

The present invention relates to coatings for dental and orthopedic implants, and in particular to coatings that incorporate nano-scale Hydroxyapatite (HAp) and nano-scale Hydroxyapatite-Zinc Oxide (HAp-ZnO) composites.

BACKGROUND ART

HAp has been widely used as a coating material for orthopedic and dental applications due to its similar chemical composition to natural bone mineral, and its capability to promote bone regeneration. Unfortunately, however, the failure of HAp-coated implants is commonly seen. It is generally believed that implant failure may be due to multiple reasons, such as poor adhesion between implant and surrounding bone and tissue, and post-implantation infections. Many studies have discussed the issues of poor osseointegration (the bonding of an orthopedic implant to juxtaposed bone) and the inability of implants to match the physical properties of surrounding bones. Currently, there is no effective solution to address the failure issue in a predictable manner, despite the significant research efforts expended in this area.

It has been reported in the literature that HAp with nano-scale crystalline features and controlled porosity and pore size could promote osseointegration. A number of methods have been developed to deposit HAp on metal implants, such as electrophoretic deposition, sputter, dip coating, spin coating, and plasma spray. It has been shown, however, that it is very challenging to produce a crystalline HAp coating with desirable coating functional features, such as surface roughness as well as controlled pore size and porosity that are retained at nanoscale. In addition, it is also necessary for nano-HAp coatings to have good adhesion strength to metallic substrates and sufficient mechanical properties for load-bearing conditions.

By using novel nano topographies, researchers have shown that nanostructured ceramics, carbon fibers, polymers, metals, and composites enhance cell functions; in particular, nanophase materials (materials with surface features less than 100 nm in at least one direction) promote osteoblast adhesion and calcium/ phosphate mineral deposition. Accordingly, nanophase materials show potential promise in improving orthopedic implant fixation. However, grain growth is one of the major issues for nanoparticle-based HAp coating when synthesized by using thermal techniques such as plasma or thermal spray methods. Additionally, brittleness and cracking are the other major issues associated with HAp coatings, though nanostructured HAp coatings are reported to be less susceptible to cracks. Typically, the cracks are due to residual stress and can cause de-bonding under external loading. As a recent development, it is reported that a textured (grooved surface, organized islands) HAp surface has shown preferentially regulated cell response, and reduced residual stresses and tendency to develop cracks. However, none of the current deposition technologies can be readily applied to achieve a coating that has spatially textured features of this type and a desired combination of passive and bioactive functions.

According to the results of a recent study, almost five times the compressive strength of bone has been achieved in bulk nanostructured HAp (879 MPa vs. 193 MPa for compacted bone), while providing roughly equivalent bending strength of bone (193 MPa vs. 160 MPa for bone), indicating the excellent potential of nanostructured HAp for dental and orthopedic implants. A nanostructured coating of HAp synthesized with an electrophoretic deposition technique showed improved adhesion and corrosion resistance for implants, though the synthesis technique experienced a shrinkage problem due to reduced particle size, leading to increased cracking susceptibility. A solution ripening technique has also been studied for minimizing this susceptibility. To address the HAp nanoparticle delivery in a hypersonic deposition, a mixture of nano-sized HAp particles and micro-sized Ti powder has been used so that the micro-sized powder served as a carrying medium. In addition, sol-gel was used for producing coatings of nanoparticles of a bioactive glass ($CaO.SiO_2.P_2O_5$) for increased bioactivity.

Of all these methods for HAp coating, each method has its own advantages over a specific processing window, but each one also has its limitations. Plasma spraying produces amorphous HAp that reduces implant durability. Also, in this process it is difficult to control particle size growth. It has been reported that electrophoretic deposition addresses the formation of amorphous HAp observed in the plasma spray process, but its follow-up consolidation process leads to an increase in cracking susceptibility due to accelerated drying shrinkage from reduced particle sizes. Also, this process is difficult to scale up. The supersonic rectangular jet impingement technique uses micron-sized titanium (Ti) powder as a carrier medium to deliver nanomaterials, which limits its direct application for nanopowders. Therefore, in addition to novel coatings, there is an equally important need for the development of new manufacturer-friendly processes for depositing nanoparticles for bio-implant coatings in general, and nanocomposite HAp coating in particular.

Zinc oxide (ZnO) has also been explored as a coating material for various biomedical applications. ZnO has been reported for its efficacy in producing an antimicrobial effect, with this effect being more pronounced for nanocrystalline ZnO. In addition, experimental results have indicated that nanophase ZnO increases osteoblast functions necessary to promote integration of orthopedic implants. To the inventors knowledge, however, ZnO has not been explored as a component of a multi-material coating for dental or orthopedic implants, or other biomedical applications.

For all the reasons set forth above, a simple and efficient method of producing a durable, high-quality coating for dental and orthopedic implants, which both promotes osseointegration and provides an anti-microbial effect, would be highly desirable.

DISCLOSURE OF THE INVENTION

In certain aspects, the present invention is directed to a novel implant coating process, combining electrostatic spray coating (ESC) with a sintering process to meet mechanical and biological requirements for next-generation dental and orthopedic implants. The coating process offers a high deposition rate, suitability for various composite coatings, compatibility with simple and complex geometries, flexibility, low energy consumption, and low cost. Experiments conducted by the inventors demonstrate that the application of this coating process may reduce or even eliminate the formation of amorphous phase HAp, which is soluble in body fluids and results in subsequent dissolution of the material before natural bone tissue integrates. The HAp nanocoatings fabricated by this coating process have the following benefits: improved adhesion strength prevents coating delamination; biomimetic chemistry to natural bone tissues (Ca/P ratio very close to natural bone); large effective surface areas enhance cell attachment and growth; nano-scale roughness enabled by nanoparticles of HAp promotes implant-tissue integration; nano-to-micron pores provide more anchor sites for inducing enhanced cell activities; a high resistance to scratching; and the highly crystalline HAp coating reduces HAp dissolution in body fluids.

While certain aspects of the present invention are directed to a coating incorporating HAp, other aspects incorporate a combination of nanocrystalline HAp and ZnO in an implant coating. Due to their compatibility and stability in composite form even at relatively high temperature, and their complementary properties in increasing osteoblast functions and antimicrobial activities, the result is a multi-functional coating for dental and orthopedic implants and other biomedical applications. The resulting coating is micro-patterned and has inter-connected nanopores, and is believed to offer osseointegration, antimicrobial activities, and a reduced tendency to form cracks.

In certain aspects, the coating incorporates antimicrobial nanostructured ZnO, with particle sizes of about 50 nm, and bioactive HAp, with particles sizes of about 100 nm. The combination material is deposited in a textured form by use of an ESC process on, for example, a titanium implant surface. The multifunctional coating that results from the combination of textured nanostructured HAp and ZnO by use of ESC and a transient microwave sintering process facilitates nanoparticle deposition while retaining the nanostructured features.

In one aspect, the invention is directed to an implant comprising a substrate and a coating material, wherein the coating material comprises HAp particles and ZnO particles, and wherein the coating material comprises a plurality of pores ranging from nano-scale pores to micro-scale pores.

In another aspect, the invention is directed to a coated implant for biomedical applications comprising a substrate and a coating, wherein the coating consists essentially of nano-sized HAp particles and nano-sized ZnO particles.

In another aspect, the invention is directed to an article comprising a coating and a substrate, wherein the coating comprises HAp particles arranged in a plurality of islands with a plurality of spaces dispersed therebetween.

In another aspect, the invention is directed to a method for manufacturing an implant comprising a substrate and a coating, wherein the coating comprises nano-sized HAp particles, the method comprising the steps of de-agglomerating the HAp particles, electrostatically spraying the HAp particles from a spray gun onto the substrate to form the coating, and sintering the implant whereby the coating is bound to the substrate, wherein the resulting coating comprises a plurality of pores with diameters in the range of nano-size to micro-size.

In another aspect, the invention is directed to a method for manufacturing an article comprising a substrate and a coating, the coating comprising nano-sized HAp particles and nano-sized ZnO particles, the method comprising the steps of de-agglomerating the particles, electrostatically spraying the particles from a spray gun onto the substrate to form the coating, and sintering the article.

These and other features, objects and advantages of the present invention will become better understood from a consideration of the following detailed description of the best mode for carrying out the invention, and the appended claims, in conjunction with the drawings as described following:

BEST MODE FOR CARRYING OUT THE INVENTION

Two preferred embodiments of the invention will be discussed below, one involving an HAp coating and the other a composite HAp-ZnO coating, but the pre-deposition and deposition processes that will be described following are generally common to both. The techniques described herein allow (1) homogeneous mixing, (2) deagglomeration, and (3) deposition and texturing followed by sintering without significant grain growth. These processes are scalable and relatively low-cost.

In the preferred embodiments, the pre-deposition process begins with ball milling. In ball milling, two main collisions are involved, one between two interacting balls, and the second between a colliding ball and the wall of the container vial. Various parametric considerations are essential, including types of balls and vials to minimize cross contamination, milling time, and charge ratio. In the preferred embodiments, ceramic vials and balls are employed to avoid cross contamination, and an inert gas medium is introduced for the ball milling. Variable parameters will be the charge ratio of nanoparticulate powders, time of milling, and rotations per minute (RPM) of milling.

After milling, the nanoparticulates may be exposed to supersonic jet milling. A jet mill employs compressed air to produce powder particles or de-agglomerate particle clusters into sizes less than a few microns. In the jet milling process, a mixing of air and particles takes place in a high velocity, turbulent flow and is characterized by significantly non-equilibrium phase velocity. This mixing process creates particle-to-particle, cluster-to-cluster impact, which refines the powder particles and partially helps to de-agglomerate large clusters of particles held mainly by adhesion forces (Van der Waals forces including dipole/dipole, dipole/non-polar, and non-polar/non-polar). Further, pulverization occurs in the engineered central chamber as the mixture is driven at near sonic velocity around the perimeter of the chamber by multiple air jets, leading to additional reduction of particle or cluster size. The process allows recirculation of over-sized particles or clusters, enhancing the incidence and the effect of collisions between particles of the process material itself, and between particles and the chamber. As particles or clusters are reduced in size and progressively lose mass, they move toward the central discharge port. Typically, in addition to air or gas quality and the physical properties (density and hardness) of the process material itself, pressure for the pushing nozzle and grinding nozzles, and mass feed rate of powder, are the major parameters affecting the resulting powders.

Figure 1:
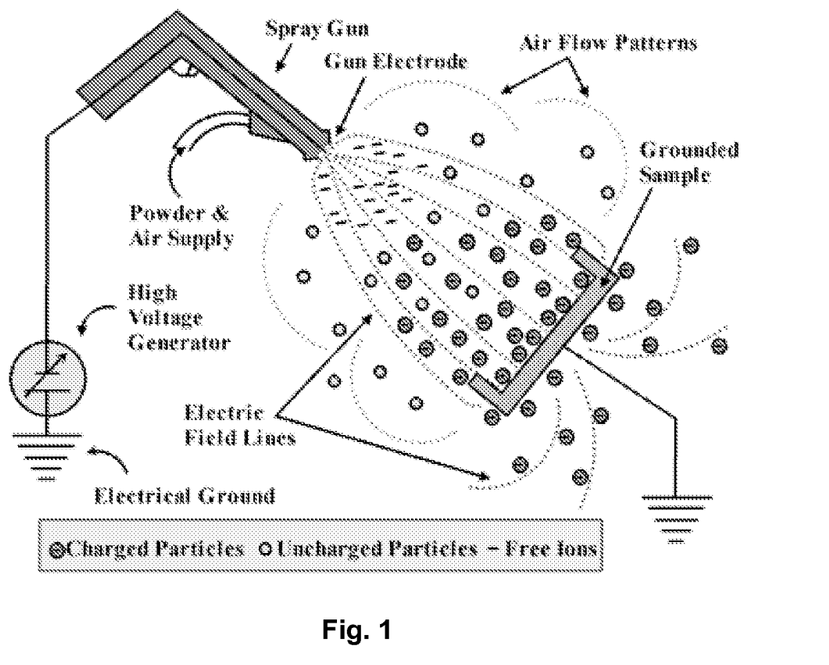
FIG. 1 is a functional schematic for the ESC system for deposition of nanoparticles according to a preferred embodiment of the present invention.
Figure 2A:
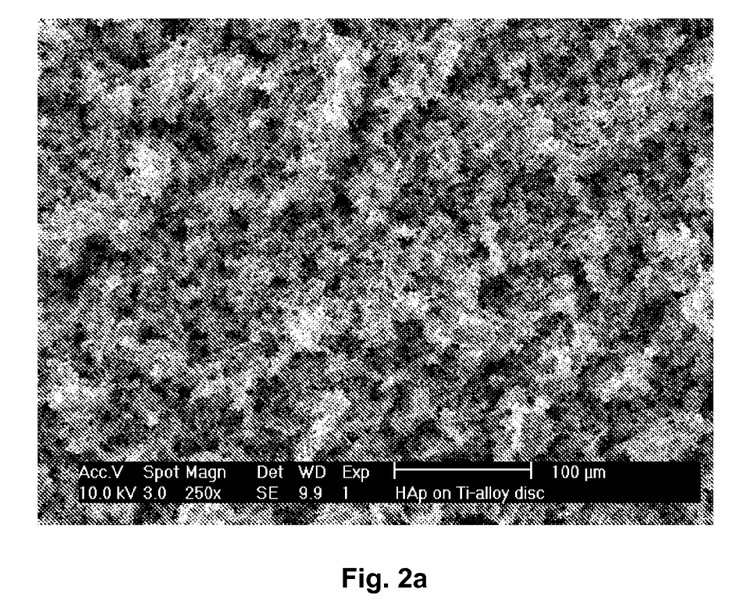
FIG. 2a is a scanning electron microscope (SEM) micrograph depicting an HAp coating preform (before microwave sintering) on Ti substrates, shown at low magnification, according to a preferred embodiment of the present invention.
Figure 2B:
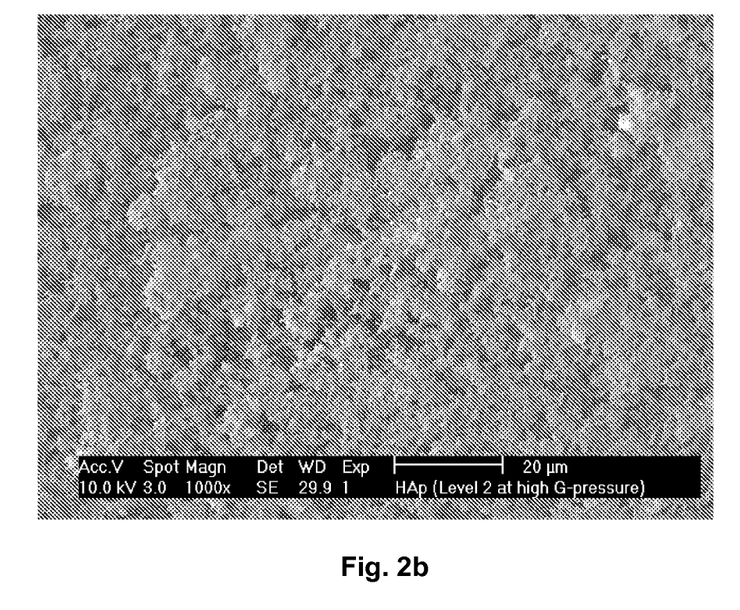
FIG. 2b is an SEM micrograph depicting an HAp coating preform (before microwave sintering) on Ti substrates, shown at medium magnification, according to a preferred embodiment of the present invention.
Figure 2C:
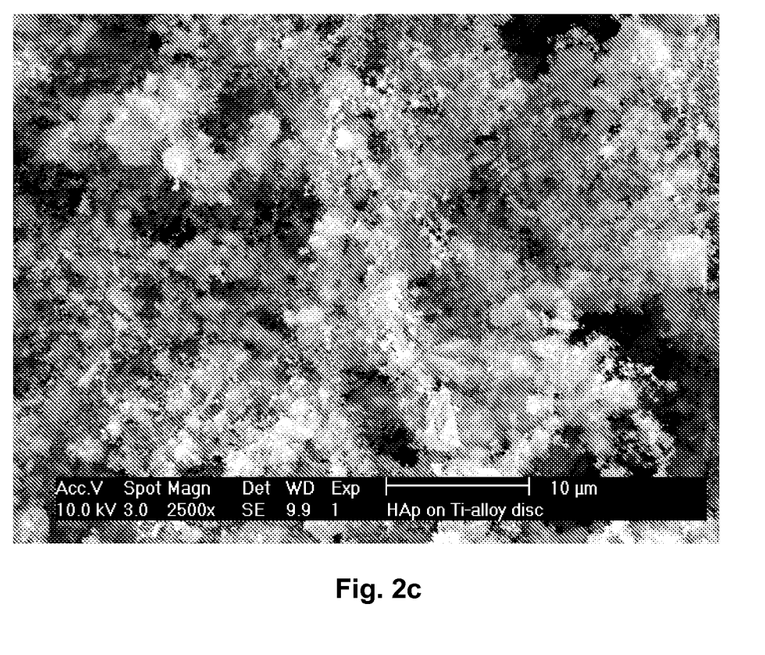
FIG. 2c is an SEM micrograph depicting an HAp coating preform (before microwave sintering) on Ti substrates, shown at high magnification, according to a preferred embodiment of the present invention.
Figure 2D:
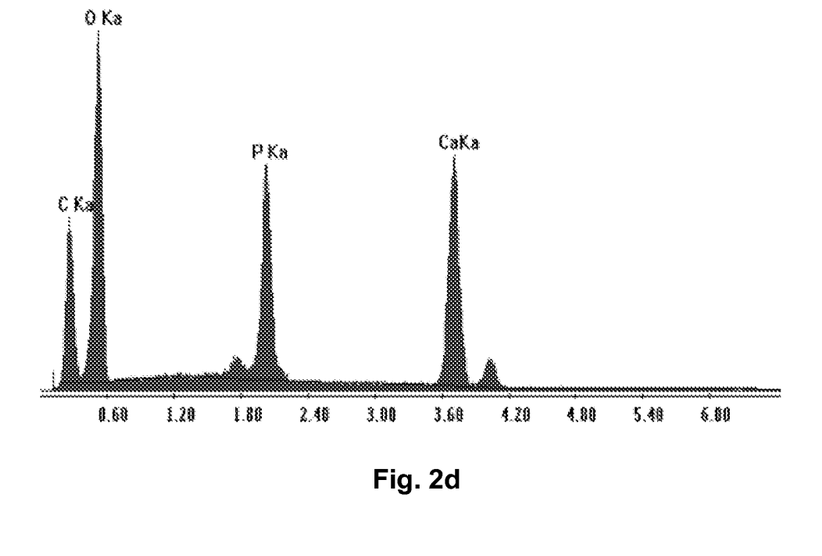
FIG. 2d is a graph depicting energy-dispersive X-ray spectroscopy (EDX) results of HAp particles before the coating process according to a preferred embodiment of the present invention.
Figure 2E:
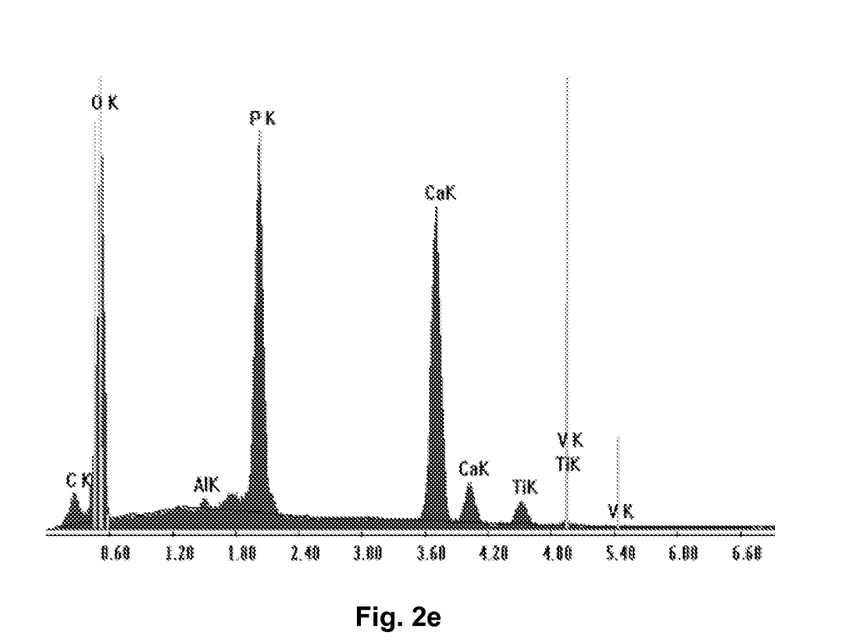
FIG. 2e is a graph depicting EDX results of HAp particles after deposition onto a Ti substrate according to a preferred embodiment of the present invention.
Figure 2F:
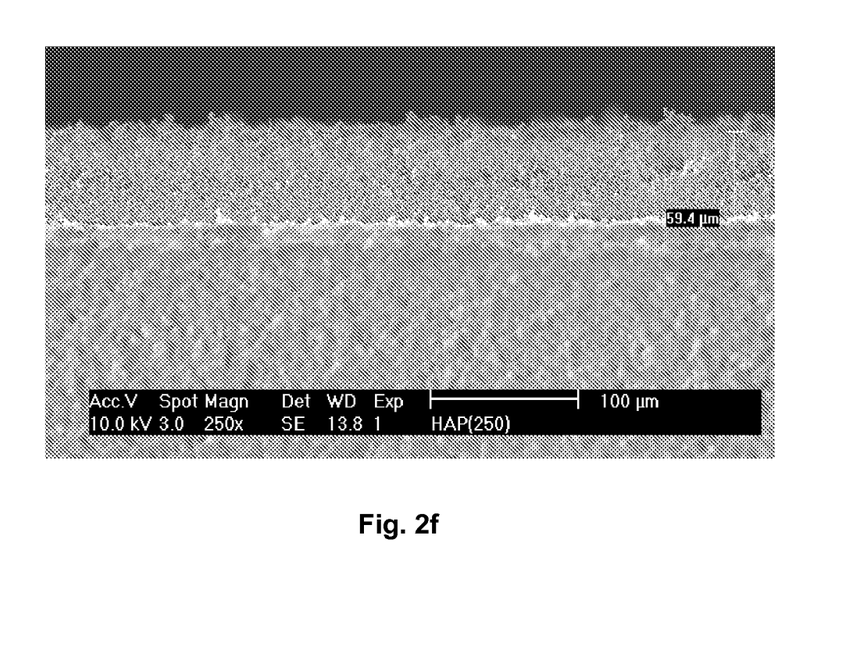
FIG. 2f is an SEM micrograph depicting an HAp nanocoating on a Ti substrate in cross-section according to a preferred embodiment of the present invention.

After the material is ball milled and then supersonic jet milled, it can be used as a feed material to the ESC unit. ESC is a process involving physical spray of nano and/or micro particulates in powder or in suspension forms. It various forms, it is widely used in the paint industry to coat materials with pigments. As shown schematically in FIG. 1, the powder particles or suspension will be charged with the same electrical polarity as they are ejected out of the spray gun and are exposed to an electrostatic field. The field is generated by a point electrode with applied voltage of typically a few tens of kilovolts (e.g., −60~−80 kV). The charged particles follow the electrostatic field lines in 3D and deposit on the grounded 3D substrates conformally. In addition, this design may offer the capability to align the nanoparticles and pattern them in a specific direction based on templates for desired properties with the assistance of an electrostatic field and shadow mask. A pre-designed shadow mask made of steel pre-form is typically aligned conformally with the Ti implant substrate. This mask is introduced in the path of trajectory of the charged nanoparticles on the way to the electrically grounded Ti implant substrate. Typically, one can deposit lines and pads as small as 100 µm in width. Optionally, an array of lines and circular pads as the starting templates can be used. This patterning will allow a further increase in the surface area while at the same time arriving at a solution to achieve intimate mechanical integrity and reliability of the coating. Further, this may provide an interconnected network of x-y axes microchannels and enhanced "mobility" of ions in the vicinity of the implant.

Another important point of ESC deposition is process control for a given material. The resulting coating thickness and uniformity are determined by material (powder or liquid suspension) feeding mass, the electrical voltage applied to the electrode, the electrode-to-substrate distance, and the main air pressure. As a combination of physical properties of the particles and parameters of the process, the charge-to-mass (q/m) ratio is an important indication of how well the particles are charged and the resulting coating efficiency. Normally, optimization is required for the process to achieve uniform deposition. Feeding mass, electrical voltage of the point electrode, mask pattern, and substrate to mask to point-electrode distance are variable parameters to achieve uniform coating thickness up to 50 µm.

Other types of coating processes may be used in alternative embodiments either in lieu of or in addition to the ESC process. For example, ultrasonic spray coating may be employed, either in place of ESC or as a post-deposition second coating technique. ESC hybrids and ESC spin-offs may be employed. In addition, multiple ESC processes may be used to achieve multiple coatings in various embodiments.

A special coated-part handling fixture may be used as the patterned nanopowder is held together on the Ti implant by electrostatic forces and needs careful handling before sintering. Microwave sintering can be performed using microwave radiation (about 2.45 GHz). In microwave sintering, heating of an isothermal disc of silicon carbide is achieved by internal absorption on which the coated representative implant substrate is placed. One can achieve high temperatures (up to 1000-1500° C.) and variable rapid heating rates and fast sintering time (as little as 5~10 minutes) for HAp coating as compared to traditional thermal heating. Use of traditional thermal heating or infrared (IR) heating poses a challenge in nanomanufacturing due to the extended time and temperature spectra allowing extended diffusion and grain growth. Nevertheless, in alternative embodiments other sintering methods, such as but not limited to pulsed infrared (IR) and laser sintering, may be employed. These sintering processes may be employed globally or selectively on the coated article. For example, local sintering could be employed if the coating is desired on only a portion of the article; after sintering, the unsintered portion of the coating could be easily removed, resulting in an article that is only partially coated.

In a first preferred embodiment for preparing a coating for a dental or orthopedic implant using the deposition techniques described above, HAp nanoparticles were used as the sole coating material, without the addition of other agents. The HAp nanoparticles are generally electrically insulating in nature and can carry the static surface charge over a distance of a few tens of centimeters. The HAp particles were charged when they exit the powder spray gun, and follow the electric field lines toward the grounded objects (Ti substrates in this example) and formed a uniform and conformal coating preform. The coating preform can be consolidated with desired chemistry and surface morphology, and reasonable adhesion achieved, by the use of a variety of processes, such as laser. The HAp coating preform is then sintered in a microwave furnace. The sintering of HA-coated Ti implants is performed in an air environment in order to achieve desirable nano-HA chemistry (Ca/P ratio of 1.60±0.06 to mimic natural bone mineral). In one set of examples, the parameters for the sintering were set at a temperature of 1000-1300° C. for 5-20 minutes.

The deposited HAp coating was characterized for grain size and pore size using an environmental scanning electron microscope (ESEM), the chemical composition and Ca/P ratio using EDX analysis, and crystalline phases using XRD analysis. Such HAp coating was further characterized for its mechanical properties, such as adhesion strength (scratch resistance), hardness, and toughness. The microscratch test method is commonly used to measure the critical load of a coating, which is directly correlated to the coating adhesion. Microscratch testing according to ASTM C1624 was carried out for HA-coated samples produced as stated above. The diamond stylus was drawn on top of each sample by using an increasing load, between 0.03N to 30 N, at constant velocity of 0.75 mm/min, until a well-defined failure occurred. The normal load under which the de-lamination of the coating from the Ti implants occurred is defined as critical load, which is typically determined by optical observation in combination with acoustic emission technique.

Human palatal mesenchymal cells were cultured in MEM Eagle Medium (EMEM) with 10% fetal bovine serum (FBS). The specimens of four different surfaces—textured titanium (TiP), HAp coating on textured titanium (HApTiP), HA coating on machined titanium (HApTiM), and a control surface (TCP) were ultraviolet (UV) sterilized for 10 minutes on each side. SEM was utilized for the study of cell morphology and its interaction with the coating surfaces after 72 hours of culture. Early matrix expression was measured using a key transcription factor for bone differentiation, cbfa-1, an early marker for the capacity for organic mineral formation, alkaline phosphatase, and a late differentiation matrix-related protein, osteocalcin.

FIG. 2 shows the results of HAp nanocoatings deposited by the ESC system described above before the microwave sintering. The HAp coating surface morphology was characterized using SEM, with different magnifications of the resulting surface shown in FIGS. 2a-2c. The chemical composition of the HAp coating before microwave sintering was characterized using EDX technology. As shown in FIG. 2e in comparison with the original HAp particles as shown in FIG. 2d, the chemical composition of the deposited HAp coating preform is consistent with that of the as—received HAp particles. The coating thickness variation was characterized using cross sections, and statistical results showed the thickness to be about 60±2.1 μm. A representative cross section of the deposited HAp nanocoating is shown in FIG. 2f.

Due to the high surface area (and thus large number of grain boundaries) of nanoparticles, size growth and chemistry control are two major challenges in sintering of the deposited HAp nanoparticles. Typically, the size growth rate is inversely proportional to grain diameter, thus, the grain growth of a sintered product from loose powder strongly depends on the initial particle average size (at time zero), and the duration of the sintering process. In addition, the onset of sintering of nanoparticles occurs at a much lower temperature partially because of high surface area, leading to better heat conduction and absorption. Therefore, a transient heating process is needed. To address this issue, sintering in a microwave furnace (3 kW, 2.45 GHz) was performed on deposited HAp nanoparticles. The sintered HAp not only retains particle size with good adhesion, but also keeps the chemistry (ratio of Ca/P) desired for implant applications.

Figure 3A:
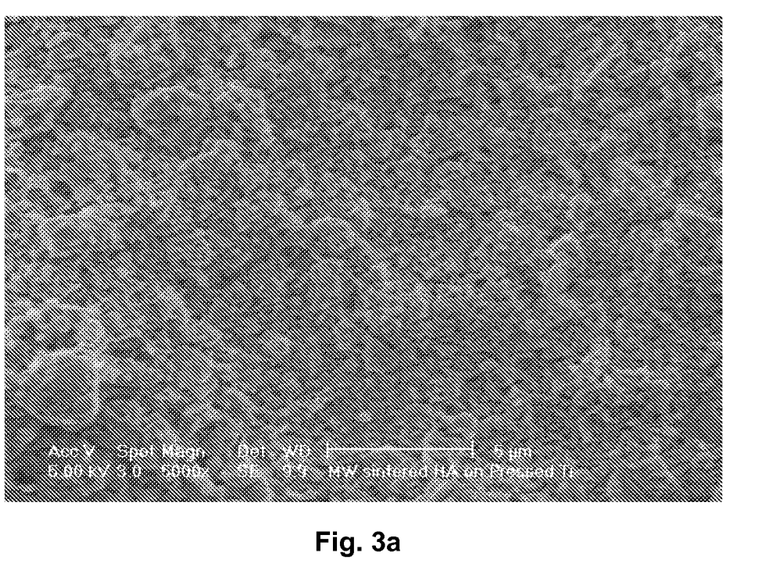
FIG. 3a is an SEM micrograph depicting an HAp coating after microwave sintering, shown at low magnification, according to a preferred embodiment of the present invention.
Figure 3B:
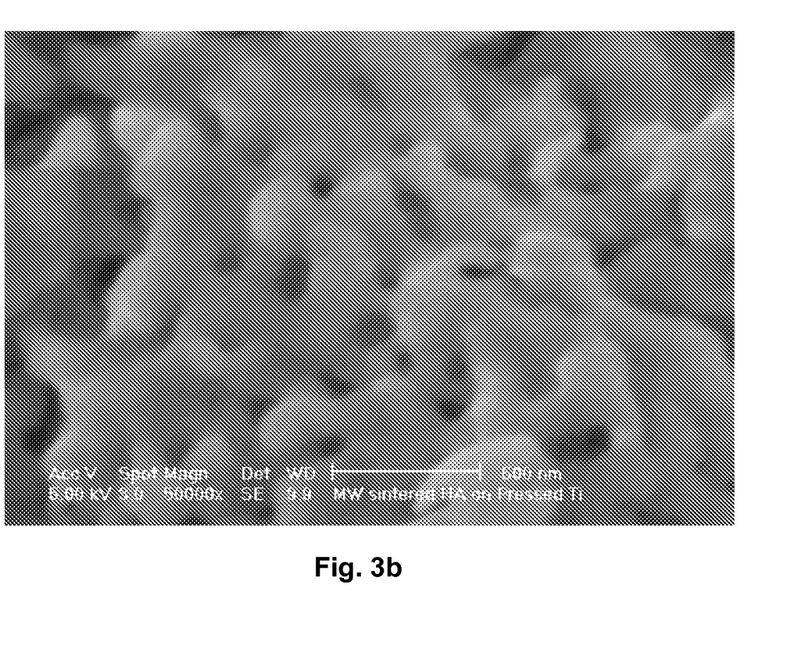
FIG. 3b is an SEM micrograph depicting an HAp coating after microwave sintering, shown at high magnification, according to a preferred embodiment of the present invention.
Figure 3C:
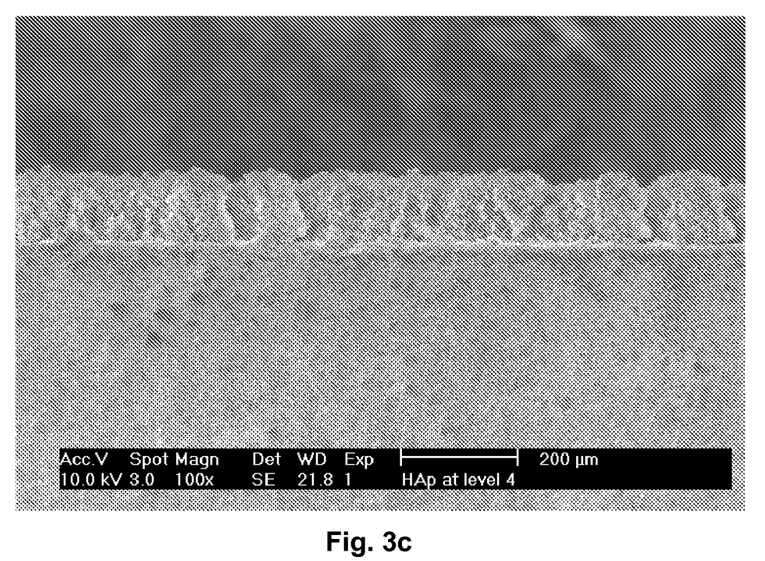
FIG. 3c is an SEM micrograph depicting an HAp coating after microwave sintering in cross-section according to a preferred embodiment of the present invention.
Figure 3D:
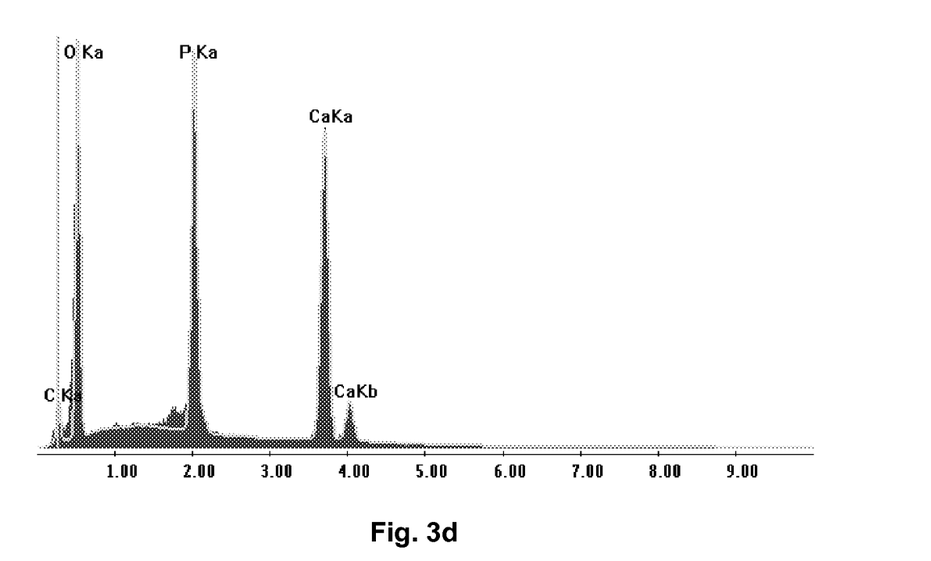
FIG. 3d is a graph depicting EDX results of an HAp nanocoating after microwave sintering according to a preferred embodiment of the present invention.
Figure 3E:
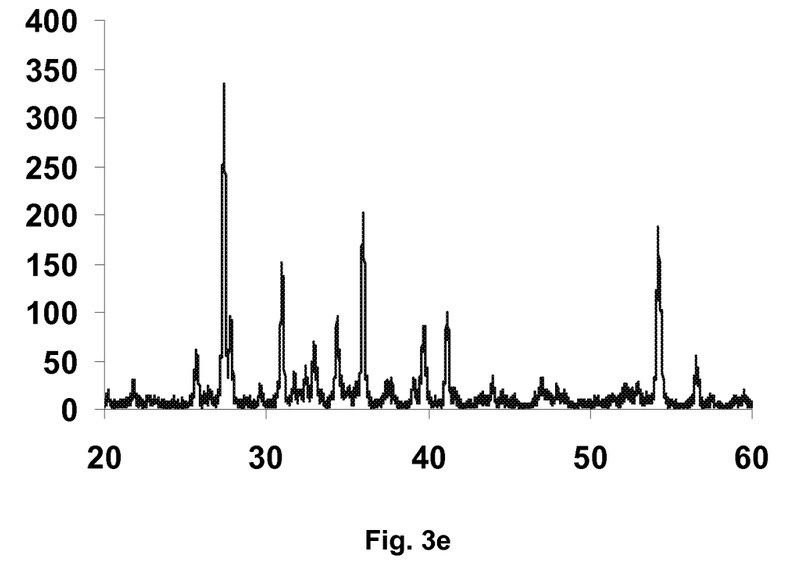
FIG. 3e is a graph depicting X-ray diffraction (XRD) results of an HAp nanocoating after microwave sintering according to a preferred embodiment of the present invention.

After the microwave sintering, the results demonstrated that a nanocrystalline HAp coating with a grain size from 50 to 300 nm and a gradient of nano-to-micron pore sizes was fabricated successfully using this novel coating process, as shown in FIGS. 3a-3c. The controlled nano-scale grain size and a gradient of pore sizes are believed to promote bone cell functions and to facilitate bone healing. EDX results shown in FIG. 3d demonstrate that the nano-HAp coating had a Ca/P ratio of about 1.6, very close to natural bone, and thus favorable for bone cell growth. XRD results confirmed that the nano-HAp coating was highly crystalline after sintering, as shown in FIG. 3e.

Optical examination at the end of the microscratch test coupled with both acoustic emission response and frictional properties variation during the test provided insight into the coating adhesion. Microscratch test results showed that the critical load of coating de-lamination reached as high as 10 N.

Figure 4A:
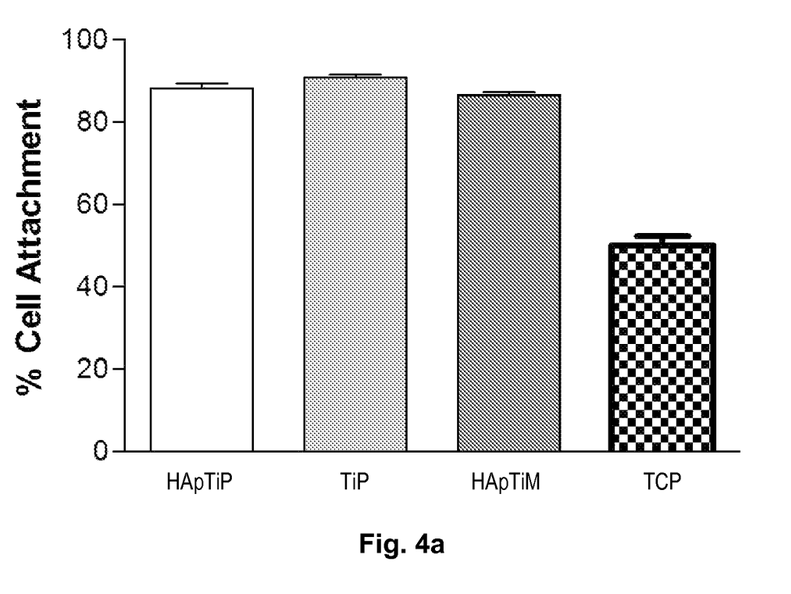
FIG. 4a is a bar graph depicting experimental results of human palatal mesenchymal cell attachment on HApTiP, TiP, HApTiM, and a control TCP surface according to a preferred embodiment of the present invention.
Figure 4B:
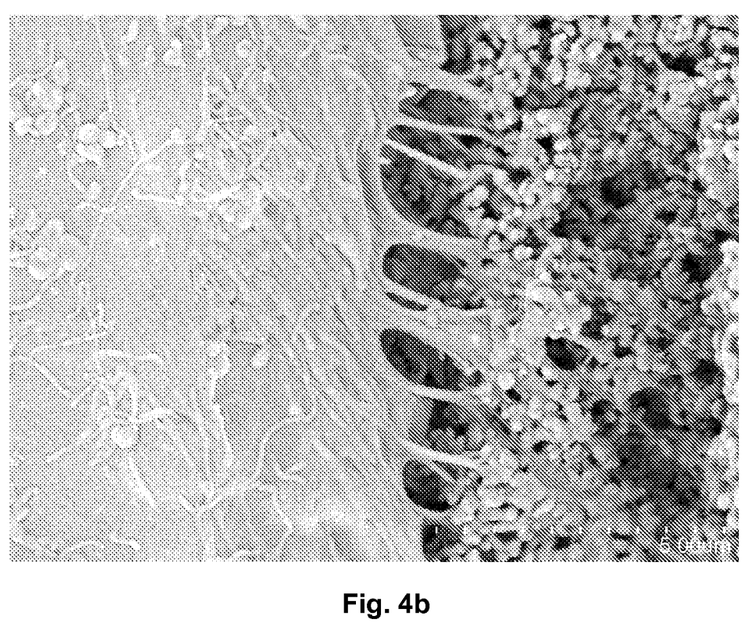
FIG. 4b is an SEM micrograph depicting cell morphology and cell interaction with an HAp-coated surface according to a preferred embodiment of the present invention.

Human palatal mesenchymal cell attachment on HAp nanocoatings were very high, with an average of 88.20±2.03% for the HATiP and 86.5±1.35% for HATiM, as shown in FIG. 4a, which suggests nano crystalline and quasi-stoichiometric HAp surfaces were capable of high degrees of cell attachment, and did not result in early cytotoxic cellular necrosis. Cell differentiation assays indicated that HAp nanocoatings were capable of high levels of cell adhesion, which, in turn, led to high level of early osteoblast (bone forming cells) gene expression. Initial in vitro results suggested positive effects of HAp nanocoatings on cell functions. FIG. 4b depicts cell morphology and cell interaction with the HAp-coated surface.

In a second preferred embodiment of the present invention, a homogenous mixture of HAp and ZnO nanoparticles are applied as a composite to a surface for implants and other biomedical applications. In overview, the process involves the following steps: (1) create the mixture of ZnO and HAp nanoparticles, (2) fluidization and deagglomeration of the nanoparticle mixture, (3) deposition of multifunctional nanoparticles and texturing of the coating, and (4) binding of the nanoparticulate coating while keeping phase, structure and texture intact.

A number of antimicrobial materials choices could be used in alternative embodiments. Silver (Ag), for example, is well known as an anti-microbial agent. ZnO is, however, used in the preferred embodiment for the following reasons: (1) zinc is well demonstrated to work in the human body to enhance the immune response; (2) ZnO in a host titanium dioxide ($TiO_2$) ceramic matrix is an effective antimicrobial agent; (3) ZnO has been found to perform in an HAp matrix to enhance densification of the HAp composite ceramic, and it will allow better mechanical strength and integrity through intra-granular bonding, and (4) the low melting temperature of silver (about 960° C.) puts serious limitations on the recommended sintering of the host HAp matrix, where sintering temperature is much higher (about 1250° C.). This melting temperature mismatch may result in serious restrictions, and force a sacrifice of the quality of the bonding due to a lack of intra-granular bonding.

Texturing refers to a porous network in the coating as well as an intentionally deposited x-y pattern. Such texturing is commonly seen in nature. For example, microbial symbiosis and air breathing in soil is accomplished in a porous network of soil particles in a fertile ground, and the surface pattern on a lotus leaf along with nano hair offers superhydrophobicity. A microscale pattern with a nanoscale porous network of channels in the coating, such as texturing, coupled with the ZnO on HAp coated orthopedic materials, enhances osseointegration, significantly reduces bacteria count, and allow excellent mechanical adhesion between implant and bone. An embodiment of the present invention includes the HAp-ZnO nanocomposite coating formed into small and organized islands such that residual stresses and cracking due to shrinkage and thermal mismatch may be reduced. The patterned HAp-ZnO nanocomposite can also promote cell organization through contact guidance, topology, and its unique cell interactions.

As may be seen from the discussion above, texturing relates to two important surface features, namely (1) an interconnected network of nano- and micro-sized pores (channels) in x-y-z axes formed during the spray deposition and microwave sintering of the HAp-ZnO nanoparticles composite, and (2) an array of microstructures (e.g., a pattern of square shaped microstructures, about 250×250 $\mu m^2$ with 50-100 $\mu m$ spacing between square structures) of HAp-ZnO nanocomposite particulate matrix intentionally deposited using ESC and a shadow mask. It is believed that this structure will result in a multifunctional interface, where bone tissues can see nanostructure, with further enhancement due to texturing surface-to-volume ratio along with HAp-ZnO nanochemistries to obtain enhanced osseointegration and antimicrobial responses, and at the same time discontinuous deposition of ceramic brittle coating, particularly on large area and/or intricate implant parts. In addition, it is believed that this textured coating may allow integration of other desired compounds, such as drugs, in particular peptide drugs, whereby the textured surface acts as a sacrificial or permanent drug delivery system. While the pattern in the texture may create microchannels for drug delivery, both the porous structure and the texture may contribute to the drug delivery aspect of the various embodiments.

In alternative embodiments, various combinations of materials and coatings may be used, in single or multiple coatings of an implant or other article. Materials employed may include, for example, HAp, ZnO, Ag, gold (Au), and titanium dioxide ($TiO_2$). These materials may be used in initial coatings or subsequent coatings, either pre- or post-sintering. For example, in a few illustrative alternative embodiments, a first HAp-based coating may be coating with a second HAp coating, or with an overcoating of Ag. Other post-sintering applications could include therapeutic drugs, particularly peptide drugs, for purposes of drug delivery. The drugs may be applied in various manners, including ESC, vapor deposition, and dipping.

The following references are hereby incorporated by reference, as if fully set forth herein:

1. Bandyopadhyay A., Bernard S., Xue W., Bose S., "Calcium Phosphate-Based Resorbable Ceramics: Influence of MgO, ZnO, and SiO2 Dopants," *Journal of the American Ceramic Society*, Vol. 89, pp. 2675 (2006).
2. Brown, W. D., Beera, R. A., Malshe, A. P., and Naseem, H. A., "Process and Apparatus For Applying Charged Particles to a Substrate, Processes For Forming a Layer on a Substrate, Products Made Therefrom", U.S. Pat. No. 6,544,599.
3. Gallardo, J., Galliano, P., Moreno, R., and Duran, A., *Journal of Sol-gel Science and Technology*, 19, pp. 107-111 (2000).
4. Huang, J., Jayasinghe, S. N., Best, S. M., Edirisinghe, M. J., Brooks, R. A., Bonfield, W. "Electrospraying of A Nano-Hydroxyapatite Suspension," *Journal of Materials Science* 39, Pp. 1029-1032 (2004).
5. Jiang, W., Li, S., Gilbert, N., Malshe, A., "Electro Spray Deposition of Nanostructured Hydroxyapatite (HAp) Coating for Biomedical Applications," *International Journal for Nanomanufacturing* (accepted 2006).
6. Klabunde K J, Strak J, Koper O, Mohs C, Park D, Decker S, Jiang Y, Lagadic I, Zhang D. Nanocrystals as stoichiometric reagents with unique surface chemistry. *J Phys Chem*, Vol. 100, pp. 12141 (1996).
7. Shukla, V., Elliott, G. S., and Kear, B. H., *Scripta Materica*, 44, pp. 2179-2182 (2001).
8. Webster T J, Ergun C, Doremus R H, Siegel R W, Bizios R, "Specific proteins mediate enhanced osteoblast adhesion on nanophase ceramics," *J Biomed Mater Res*, Vol. 52, pp. 475 (2000).
9. Webster T J, "Nanophase ceramics: The future of orthopedic and dental implant material," In: Ying J Y, editor. *Nanostructured Materials*, New York: Academy Press; pp 125-166 (2001).
10. Webster T J, Schadler L S, Siegel R W, Bizios R, "Mechanisms of enhanced osteoblast adhesion on nanophase alumina involve vitronectin," *Tissue Eng*, Vol. 7, pp. 291 (2001).
11. Webster T J, Ergun C, Dorenus R H, Seigel R W, Bizios R., "Enhanced osteoclast-like functions on nanophase ceramics," *Biomaterials*, 22:1327-1333 (2001).
12. Wei, M., Ruys, A. J., Milthorpe, B. K., and Sorrell, C. C., *Journal of Biomedical Materials Research*, 45(1), pp. 11-19 (1999).
13. Zhang, Zongtao, Dunn, Mattew F., Xiao, T. D., Tomsia, Atoni P., and Siaz, E., *Materials Research Society Proceedings*, 703, pp. 291-296 (2002).

As used herein, "comprising" is synonymous with "including," "containing," or "characterized by," and is inclusive or open-ended and does not exclude additional, unrecited elements or method steps. As used herein, "consisting of" excludes any element, step, or ingredients not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims. Thus, additional embodiments are within the scope of the invention and within the following claims.

In general the terms and phrases used herein have their art-recognized meaning, which can be found by reference to standard texts, journal references and contexts known to those skilled in the art. The preceding definitions are provided to clarify their specific use in the context of the invention.

All references cited herein are hereby incorporated by reference to the extent that there is no inconsistency with the disclosure of this specification.

The present invention has been described with reference to certain preferred and alternative embodiments that are intended to be exemplary only, and not limiting to the full scope of the present invention as set forth in the appended claims.

The invention claimed is:

1. A medical implant comprising a substrate and a coating material deposited directly onto the substrate,
wherein the coating material comprises a sintered homogenous mixture of HAp nanoparticles with a grain size of about 50 nm to about 300 nm consisting essentially of HAp and ZnO particles consisting essentially of ZnO, and
wherein the coating material comprises an interconnected network of pores ranging from nano-scale pores to micro-scale pores extending along the x-, y-, and z-axes, and an array of projecting square-shaped microstructures that are about 250 μm on a side and with intersecting channel-shaped spaces therebetween having a width of about 50 to 100 μm.

2. The medical implant of claim 1, further comprising a second coating material on top of the coating material.

3. The medical implant of claim 2, wherein the second coating material comprises a material selected from the group consisting of HAp, ZnO, Ag, Au, and $TiO_2$.

4. The medical implant of claim 1, further comprising a therapeutic drug applied to the coating.

5. The medical implant of claim 1, wherein the coating material comprises a surface texture.

6. The implant of claim 1, wherein the coating material demonstrates a critical load of delamination of at least 10 N.

7. The implant of claim 1, wherein the coating material comprising a surface area configured to bond to a plurality of cell tissues along at least 85% of the surface area.

8. A method for manufacturing the medical implant of claim 1 comprising a substrate and a coating material deposited directly onto the substrate, wherein the coating comprises nano-sized HAp particles, the method comprising the steps of de-agglomerating the HAp particles; spraying the HAp particles from a spray gun onto the substrate to form the coating; and sintering the implant whereby the coating is bound to the substrate, wherein the resulting coating comprises a plurality of pores with dimensions in the range of nano-size to micro-size.

9. The method of claim 8, wherein the sintering step comprises microwave sintering.

10. The method of claim 8, wherein the de-agglomerating step comprises the step of ball milling.

11. The method of claim 8, wherein the de-agglomerating step comprises the step of jet milling.

12. The method of claim 11, wherein the de-agglomerating step further comprises the step of ball milling.

13. The method of claim 8, wherein a mask is introduced between the spray gun and the substrate before the electrostatically spraying step.

14. The method of claim 8, wherein the HAp particles comprise a dimension in the range of about 50 nm to about 300 nm.

15. The method of claim 8, wherein the resulting coating comprises a textured surface.

16. The method of claim 8, wherein the coating comprises a plurality of islands of nano-sized particles.

17. The method of claim 16, wherein the islands comprise a side length of about 250 μm.

18. The method of claim 17, wherein a distance between the islands is in the range of about 50 μm to about 100 μm.

19. The method of claim 8, wherein the pores range in dimension from less than 100 nm to more than 1 μm.

20. The method of claim 8, further comprising a step of infiltrating the coating with a compound that can be leached when the implant is implanted in to a living organism.

21. The method of claim 8, wherein said spraying step is performed by means of a spraying method selected from the group consisting of ESC, an ESC hybrid method, and an ESC spin-off method.

* * * * *